United States Patent [19]
Tigwell et al.

[11] 4,288,206
[45] Sep. 8, 1981

[54] AUTOMATIC MULTIPLE WATER SAMPLER

[76] Inventors: David C. Tigwell, 401 E. Colorado, Urbana, Ill. 61801; David J. Schaeffer, 1716 E. Walnut St., Chatham, Ill. 62629

[21] Appl. No.: 66,518

[22] Filed: Aug. 15, 1979

[51] Int. Cl.³ .................. F04B 7/00; F04B 21/08
[52] U.S. Cl. ...................... 417/517; 73/864.17
[58] Field of Search ............ 73/425.6, 425.4 R; 417/516–518, DIG. 1

[56] References Cited
U.S. PATENT DOCUMENTS

| | | | |
|---|---|---|---|
| 2,515,956 | 7/1950 | Greenberg | 417/DIG. 1 |
| 2,541,086 | 2/1951 | Moule | 417/517 |
| 2,696,174 | 12/1954 | Cozzoli | 417/517 |
| 3,098,480 | 7/1963 | Worthington | 417/517 |
| 3,259,077 | 7/1966 | Wiley et al. | 417/517 |
| 3,572,130 | 3/1971 | Goldsmith | 73/425.6 |
| 4,006,847 | 2/1977 | Dooley | 222/309 |
| 4,141,469 | 2/1979 | Lee | 73/425.6 |

FOREIGN PATENT DOCUMENTS 2005374 12/1969 France .................. 73/425.6

Primary Examiner—William L. Freeh
Attorney, Agent, or Firm—Leydig, Voit, Osann, Mayer & Holt, Ltd.

[57] ABSTRACT

A water sampler for delivering simultaneous multiple samples in which the samples are taken and discharged by a plurality of glass chambered syringes driven by a crank with water flow being controlled by a glass chambered valve having a valve spool shifted under the control of the crank.

1 Claim, 1 Drawing Figure

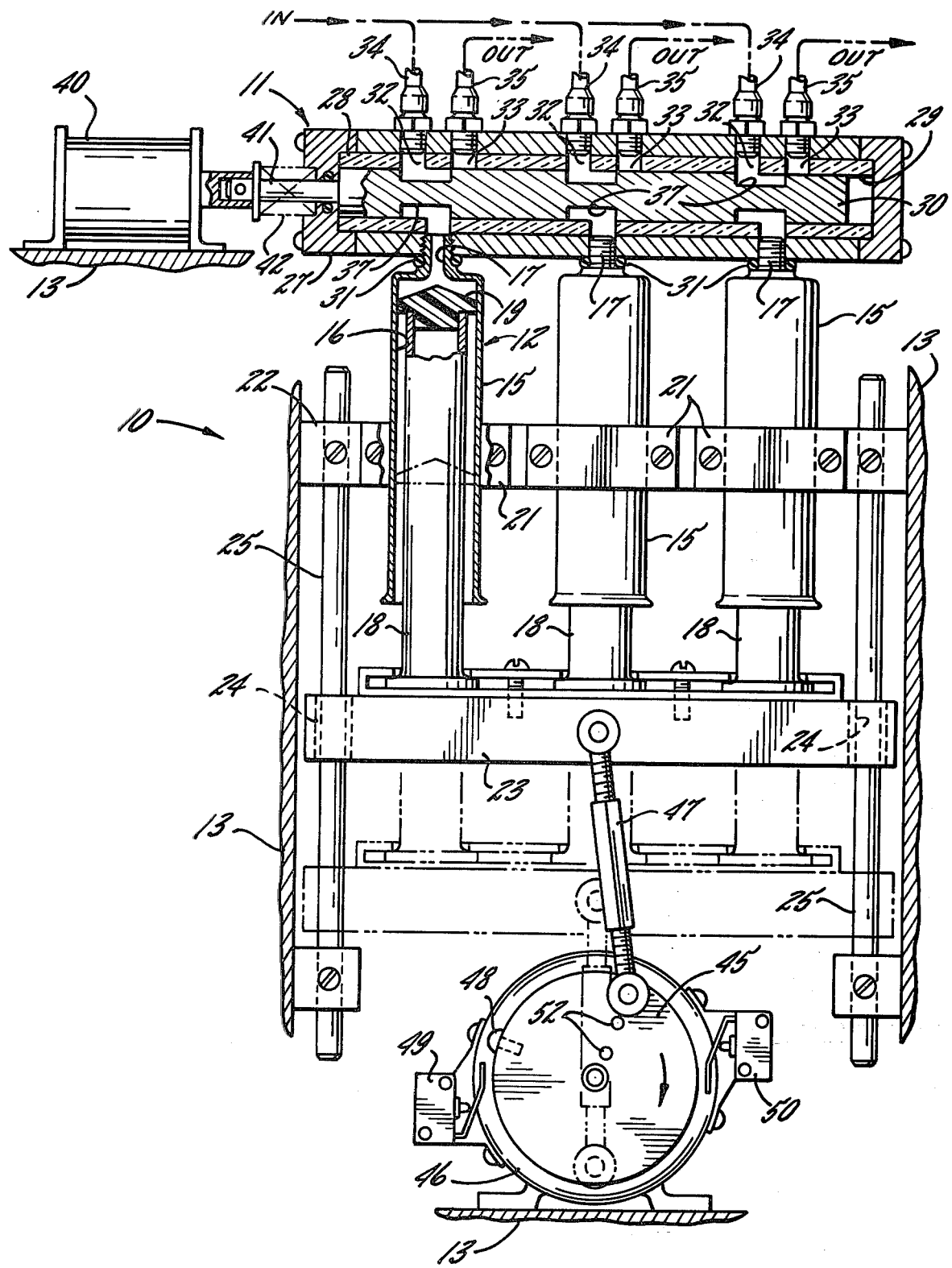

AUTOMATIC MULTIPLE WATER SAMPLER

This invention relates generally to sampling pumps and more particularly concerns an automatic water sampler providing multiple samples from a source.

The great present day concern for the quality of naturally flowing water has produced a need for devices to monitor water quality, often in remote locations and for extended periods. Various testing strategies are available, ranging from simple storage of samples for later analysis to directing samples through sorption columns designed to isolate even trace amounts of organic impurities such as pesticides, vinyl chloride, benzenes and other possible industrial wastes.

It is the primary aim of the present invention to provide a water sampler suitable for taking and delivering discrete water samples, under pressure, for testing. Because the samples are delivered under pressure, the sampler is well suited for use with sorption columns. A related object of the invention is to provide such a sampler that is capable of simultaneously delivering multiple water samples so that different testing strategies can be simultaneously followed.

It is also an object of the invention to provide a sampler of the above kind which can be readily adjusted for both sample size and for the rate at which samples are taken. Another object is to provide a sampler as characterized above which has only inert materials in contact with the water being sampled, but which utilizes standard components for economy and convenience in servicing.

A further object is to provide a sampler of the above character which functions well even when handling relatively dirty water since the critical parts are virtually self-cleaning.

Other objects and advantages of the invention will become apparent upon considering the following detailed description and upon reference to the drawing, which is:

An elevation, partially sectioned and partially schematic, of an apparatus embodying the present invention.

While the invention will be described in connection with a preferred embodiment, it will be understood that we do not intend to limit the invention to that embodiment. On the contrary, we intend to cover all alternatives, modifications and equivalents as may be included within the spirit and scope of the invention as defined by the appended claims.

Turning to the drawing, there is shown a sampler 10 embodying the invention and having a valve assembly 11 and syringe assembly 12 mounted in a housing or frame 13. The assembly 12 includes a plurality of syringes 15, three in the illustrated sampler 10, which are of standard commercial type having glass chambers 16 with opening necks 17, and plungers 18 with pistons 19 slidably fitted in the chambers 16. The pistons 19 are preferably formed of non-wetting plastic like polytetrafluoroethylene, i.e., "Teflon".

In carrying out the invention, the syringes 15 are held by blocks 21 secured to a cross bar 22 on the frame 13, and the plungers 18 are releasably secured to a drive bar 23 mounted in the frame 13 for tightly confined linear reciprocation. In the illustrated embodiment, the drive bar 23 has bushings 24 which are slidably fitted on rods 25 fixed in parallel relationship on the frame 13 so that the bar 23 is confined for reciprocation in a path parallel to the axes of the syringes 15.

In keeping with the invention, the valve assembly 11 includes a housing 27 containing a glass tube 28 defining a valve chamber 29 in which a valve spool 30 is shiftably mounted. The valve chamber 29 is opened to each of the syringes through the necks 17, and O-rings 31 provide seals between the syringes and the valve assembly 11. The valve assembly 11 and glass tube 28 also have inlet openings 32 and outlet openings 33 for each of the syringes 15, and the inlet openings 32 are connected by a common line 34 to the source of the water being sampled. The outlet openings 33 are connected by lines 35 to independent devices such as a holding vessel to store samples for later analysis or sorption columns designed to isolate one or more specific possible impurities.

Preferably, the spool 30 is formed of non-wetting plastic as are the syringe pistons 19, and the spool 30 is also formed with relieved regions 37 for alternately connecting the syringe chambers 16 with the inlet and outlet openings 32, 33, respectively. In the position illustrated, the inlet openings 32 are connected to the syringes 15. Upon shifting movement of the spool 30 to the right in the drawing, the spool relieved regions 37 couple the outlet openings 33 to the syringes 15. In the preferred embodiment, the glass tube 28 and the spool 30 are cylindrical, and the spool portions defining the outer edges of the relieved portions 37 are slightly flared in diameter to define lips having firm wiping contact with the glass tube 28.

In the illustrated embodiment, the valve spool 30 is shifted by a solenoid 40 coupled to a rod-like extension 41 of the spool. The solenoid 40 acts like a locking relay, which, when energized, shifts the spool 30 to the right in the drawing against the bias of a spring 42, whereupon the solenoid is latched. When the latch, not shown, is released the spring 42 shifts the spool 30 to the left and into the position illustrated.

For driving the bar 23 and timing the operation of the solenoid 40, a crank 45 is journaled on a support 46 mounted on the frame 13. The crank 45 is connected by a crank arm 47 to the bar 23 and is also provided with a lobe 48 that actuates a pair of microswitches 49 and 50 mounted on the support 46. The crank arm 47 is adjustable in length, being formed like a turnbuckle, and the lower end can be mounted in alternate mounting holes 52 in the crank 45 for adjusting the throw of the crank and thus the distance the plungers 18 move in the syringe chambers 16 during each stroke. In the position illustrated, the lobe 48 has just tripped the switch 49 so as to release the solenoid 40 and allow the spring 42 to shift the spool 30 to the left. As the crank 45 continues to rotate clockwise, the pistons 19 will be drawn downwardly, pulling a precise, discrete sample volume into each of the syringes 15. At the bottom of the crank stroke, the switch 50 will be actuated to energize the solenoid 40 and shift the spool to the right. Further rotation of the crank 45 will lift the plungers 18 to drive the sample volumes in each of the syringes 15 through the outlet openings 33.

Use of the latching solenoid 40 to control the valve assembly 11 assures rapid changes in valve position and thus accurate control of the sample volumes being taken.

Because the samples are discharged under pressure, the sampler 10 is well suited for forcing the samples into and through a sorption column. If desired, at the end of a run, the inlet line 34 can be connected to a supply of suitable solvent and the sampler cycled to drive the desired volume of solvent through the column that has been isolating and collecting the impurity being tested for.

The crank 45 can be driven in any desired fashion, as for example, by a timing motor internal to the sampler 10 or by an external water flow meter that would cycle the sampler at desired incremental flow volumes.

It can be seen that the water being sampled contacts only inert glass and plastic, and the glass of the syringes and the glass tube 28 of the valve assembly 11 constitute mechanically stable parts coacting with the plastic parts which have a tendency to flow. This avoids the possibility of leakage from plastic deformation that exists if plastic is sealed against plastic as movable valve elements.

Those skilled in the art will readily see that the sampler 10, utilizing conventional syringes, can be economically manufactured and serviced, while providing quite precise sample volumes. The sliding of the pistons 19 in the glass chambers 16 and of the spool 30 in the glass tube 28 makes these parts virtually self-cleaning so that the sampler 10 is well suited for reliable use in relatively dirty water.

We claim as our invention:

1. A sampler for delivering multiple independent water samples comprising, in combination, a frame, a drive bar mounted in said frame for linear reciprocation, a plurality of glass chambered syringes having movable plungers mounted in said frame with their axes parallel to the direction of said bar reciprocation, said plungers being coupled to said drive bar, a valve body on said frame having a chamber opening to the chambers of said syringes, said body having an inlet and an outlet opening for each of said syringes, a valve spool shiftably mounted in said valve body chamber and having relieved regions for alternately connecting said syringe chambers with said inlet and then said outlet openings upon shifting of said spool, and means for reciprocating said drive bar and shifting said spool so that said syringe will draw liquid from said inlet openings and then positively discharge that liquid through said outlet openings, said plungers having non-wetting plastic pistons in wiping contact with said glass chambers, said valve body chamber being defined by a glass tube, and said valve spool being formed of non-wetting plastic.

* * * * *